United States Patent
Van Der Heiden

(10) Patent No.: US 8,044,273 B2
(45) Date of Patent: Oct. 25, 2011

(54) PEPPER HYBRID E 499526

(75) Inventor: Anton Arnold Van Der Heiden, Enkhuizen (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 1066 days.

(21) Appl. No.: 11/776,013

(22) Filed: Jul. 11, 2007

(65) Prior Publication Data

US 2009/0019600 A1      Jan. 15, 2009

(51) Int. Cl.
*A01H 5/00*   (2006.01)
*A01H 5/08*   (2006.01)
*A01H 5/10*   (2006.01)
*A01H 1/00*   (2006.01)
*C12N 5/04*   (2006.01)

(52) U.S. Cl. ............ 800/317.1; 800/265; 800/278; 435/421; 435/430; 435/430.1

(58) Field of Classification Search ............ None
See application file for complete search history.

(56) References Cited

U.S. PATENT DOCUMENTS

| | | | |
|---|---|---|---|
| 5,523,520 A | 6/1996 | Hunsperger et al. | |
| 5,959,186 A * | 9/1999 | Arevalos et al. | 800/317.1 |
| 6,498,287 B2 * | 12/2002 | Nash | 800/317.1 |

FOREIGN PATENT DOCUMENTS

VA    20070853    6/2009

OTHER PUBLICATIONS

Eshed, et al., 1996. Less-than-additive epistatic interactions of quantitative trait loci in tomato. Genetics 143:1807-1817.
Kraft, et al., 2000. Linkage disequilibrium and fingerprinting in sugar beet. Theor. App. Genet. 101:323-326.
Poehlman, J.M. and Sleper, D.A., Methods in Plant Breeding, In Breeding Field Crops, 4$^{th}$ ed. (1995), Iowa State University Press, pp. 172-174.

* cited by examiner

*Primary Examiner* — David T Fox
(74) *Attorney, Agent, or Firm* — Jondle & Associates, P.C.

(57) ABSTRACT

Hybrid pepper cultivar designated 'E 499526' which is a Sweetbite type and suitable for covered cultivation and open field, is disclosed. The invention relates to the seeds of hybrid pepper cultivar 'E 499526' and to the plants of hybrid pepper cultivar 'E 499526'. The invention also relates to methods for producing a pepper plant, either inbred or hybrid, by crossing the hybrid cultivar 'E 499526' with itself or another pepper cultivar. The invention further relates to methods for producing other pepper cultivars derived from the hybrid 'E 499526'.

15 Claims, No Drawings

PEPPER HYBRID E 499526

BACKGROUND OF THE INVENTION

The present invention relates to a new and distinctive pepper (*Capsicum annuum*) hybrid designated 'E 499526'. Pepper hybrid 'E 499526' produces fruit which is very small jalapeno pepper size) but mild. In addition, the plants are suitable for covered cultivation and open field growing. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The selected germplasm is crossed in order to recombine the desired traits and through selection varieties or parent lines are developed. The goal is to combine in a single variety or hybrid an improved combination of desirable traits from the parental germplasm. These important traits may include higher yield, field performance, fruit and agronomic quality such as fruit shape and length, resistance to diseases and insects, and tolerance to drought and heat.

The bell pepper (*Capsicum annuum*) originated in Mexico and the neighboring areas of Central America. Soon after Columbus' discovery of this plant, it was grown worldwide and used as a spice and a medicine. Today, pepper plants can be found growing wild in tropical areas around the world. Many countries grow it as a crop. Many of the hot peppers can be found in Latin America and China, but the US prefers sweet bell peppers. Peppers are used for fresh consumption, and they are processed into powders, sauces, and salsas. Many of the new cultivars grown today can be traced back to the early plants.

The genus *Capsicum* and species *annuum* includes most of the peppers grown in the U.S. These can be further grouped into two broad categories: chile peppers which are pungent (hot) and sweet peppers which are non-pungent (mild). The U.S. produces 4 percent of the world's capsicum peppers (sweet and hot), ranking sixth behind China, Mexico, Turkey, Spain and Nigeria. Bell peppers are the most common sweet pepper and are found in virtually every retail produce department. Grown commercially in most states, the U.S. industry in largely concentrated in California and Florida, which together accounted for 78% of output in 2000. New Jersey, Georgia and North Carolina round out the top five producing states. (Economic Research Service, USDA. Vegetables and Melons Outlook/VGS-288/Dec. 14, 2001.)

Bell peppers are eaten raw, cooked, immature and mature. Often nutritional content is altered by the changes in the way they are consumed. Per capita consumption of bell peppers in 1995 was 6.2 pounds. They are an excellent source of Vitamin C, Vitamin A, and Calcium. Red peppers have more of these qualities than the immature green peppers.

Peppers grown in temperate regions are herbaceous annuals, but are herbaceous perennials where temperatures do not drop below freezing. Pepper plants' growth habit may be prostrate, compact, or erect, but it is determinate in that after it produces nine to eleven leaves a single stem terminates in flowers. These plants are grown for the edible fleshy fruit produced by this dichotomous growth. Peppers are non-climacteric which means they do not produce ethylene. They need to stay on the vine to continue the ripening process. A deep taproot will form if the plant root system is uninjured during transplanting. The spindle root will develop fibrous secondary root systems spreading laterally and downward. On the soil surface the stem will produce adventitious roots, but not as easily as tomatoes. The leaves of the pepper plant arise singly and are simple, entire, and asymmetrical. Typical of all *Solanaceous* plants, the leaves are arranged alternately on the stem. They are shiny and glabrous and vary in shape from broadly ovate to ovate lanceolate. The flowers develop singly or in twos or threes continuously as the upper structure of the plant proliferates. The corolla is white and five lobed while the anthers are bluish or yellowish in color. The flowers have an open anther formation and will indefinitely self-pollinate. They are also pollinated by insects, which increases the chances of cross-pollination. Unlike tomatoes, whose pollen becomes nonviable in high temperatures, the pepper flowers' pollen is not extremely heat sensitive and it remains viable up to 100° Fahrenheit producing fruit throughout the season.

The fruit of a pepper plant is classified as a berry with colors from green, yellow, red, purple, black, brown, white and orange. Green is an immature fruit, yet commonly eaten this way, and as the fruit matures it changes color. In most commercial cultivars color changes are from green to red, green to yellow or green to orange. Usually, fruits of the purple and white varieties have these colors as they develop, and therefore do not have a green stage. For fruit to set, the ovaries need to be fertilized. Auxin is then produced by the seeds, which determine fruit cell elongation. The number of seeds fertilized will determine the size and shape of the fruit. The seed develop on the interior and attach to the veins. Fully developed seed is kidney shaped. There are about 4,500 seeds per ounce.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from five to ten years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of pepper plant breeding is to develop new, unique and superior pepper cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line having the same pepper traits.

Each year, the plant breeder selects the germplasm to advance to the next generation. This germplasm is grown under different geographical, climatic and soil conditions, and further selections are then made, during and at the end of the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior pepper cultivars.

The development of commercial pepper cultivars requires the development of pepper parental lines, the crossing of these lines, and the evaluation of the crosses. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max*) p 6.131-6.138 in S. J. O'Brien (ed) *Genetic Maps: Locus Maps of Complex Genomes*, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., *Theor. Appl. Genet* 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into pepper varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company, 1993.

The production of double haploids can also be used for the development of homozygous lines in a breeding program. Double haploids are produced by the doubling of a set of chromosomes from a heterozygous plant to produce a completely homozygous individual. For example, see Wan et al., *Theor. Appl. Genet.*, 77:889-892, 1989.

Descriptions of other breeding methods that are commonly used for different traits and crops can be found in one of several reference books (e.g., *Principles of Plant Breeding* John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Pepper is an important and valuable field crop. Thus, a continuing goal of plant breeders is to develop stable, high yielding pepper hybrids that are agronomically sound. The reasons for this goal are obviously to maximize the amount of fruit produced on the land used as well as to improve the fruit agronomic qualities. To accomplish this goal, the pepper breeder must select and develop pepper plants that have the traits that result in superior parental lines for producing hybrids.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a hybrid pepper designated 'E 499526'. This invention thus relates to the seeds of hybrid pepper 'E 499526', to the plants of pepper 'E 499526' and to methods for producing a pepper plant produced by crossing the hybrid cultivar 'E 499526' with itself or another pepper cultivar, and to methods for producing a pepper plant containing in its genetic material one or more transgenes and to the transgenic pepper plants produced by that method. This invention also relates to methods for producing other pepper cultivars derived from hybrid pepper cultivar 'E 499526' and to the pepper cultivars derived by the use of those methods. This invention further relates to pepper seeds and plants produced by crossing the hybrid cultivar 'E 499526' with another pepper cultivar.

Parts of the pepper plant 'E 499526' are also provided, such as e.g., fruits, leaves, stems, flowers, pollen and ovules.

In another aspect, the present invention provides regenerable cells for use in tissue culture of pepper plant 'E 499526'. The tissue culture will preferably be capable of regenerating plants having the physiological and morphological characteristics of the foregoing pepper plant, and of regenerating plants having substantially the same genotype as the foregoing inbred pepper plant. Preferably, the regenerable cells in such tissue cultures will be produced from embryo, protoplast, meristematic cell, callus, pollen, leaf, stem, petiole, root, root tip, fruit, seed, flower, anther, pistil or the like. Still further, the present invention provides pepper plants regenerated from tissue cultures of the invention.

Another aspect of the invention is to provide methods for producing other pepper plants derived from pepper cultivar 'E 499526'. Pepper cultivars derived by the use of those methods are also part of the invention.

In another aspect, the present invention provides for single gene converted plants of 'E 499526'. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, or improved agronomic quality. The single gene may be a naturally occurring pepper gene or a transgene introduced through genetic engineering techniques.

The invention further provides methods for developing pepper plants in a pepper plant breeding program using plant breeding techniques including recurrent selection, backcrossing, pedigree breeding, restriction fragment length polymorphism enhanced selection, genetic marker enhanced selection and transformation. Marker loci such as restriction fragment polymorphisms or random amplified DNA have been published for many years and may be used for selection (See Pierce et al., *HortScience* (1990) 25:605-615, Wehner, T., *Cucurbit Genetics Cooperative Report*, (1997) 20: 66-88 and Kennard et al., *Theorical Applied Genetics* (1994) 89:217-224). Seeds, pepper plants, and parts thereof produced by such breeding methods are also part of the invention.

In addition to the exemplary aspects and embodiments described above, further aspects and embodiments will become apparent by reference by study of the following descriptions.

DEFINITIONS

In the description and tables that follow, a number of terms are used. In order to provide a clear and consistent understanding of the specification and claims, including the scope to be given such terms, the following definitions are provided:

Allele. "Allele" means any of one or more alternative forms of a gene, all of which relate to one trait or characteristic. In a diploid cell or organism, the two alleles of a given gene occupy corresponding loci on a pair of homologous chromosomes.

Backcrossing. "Backcrossing" means a process in which a breeder repeatedly crosses hybrid progeny back to one of the parents, for example, a first generation hybrid $F_1$ with one of the parental genotype of the $F_1$ hybrid.

Covered cultivation. Any type of cultivation where the plants are not exposed to direct sunlight. The covering includes but is not limited to greenhouses, glasshouses, nethouses, plastic houses and tunnels.

Essentially all the physiological and morphological characteristics. A plant having essentially all the physiological and morphological characteristics means a plant having the physiological and morphological characteristics of the recurrent parent, except for the characteristics derived from the converted gene.

Internode. An "internode" means the stem segment between nodes.

Propagate. To "propagate" a plant means to reproduce the plant by means including, but not limited to, seeds, cuttings, divisions, tissue culture, embryo culture or other in vitro method.

Quantitative Trait Loci (QTL). "Quantitative trait loci" refer to genetic loci that control to some degree numerically representable traits that are usually continuously distributed.

Regeneration. "Regeneration" refers to the development of a plant from tissue culture.

Single gene converted. "Single gene converted" or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Sweetbite. "Sweetbite" means any sweet pepper plant having fruit with 2 or 3 locules, conical shaped, with a diameter between 1.5 centimeters and 3 centimeters and a length between 3 centimeters and 7 centimeters.

Transgene. A "transgene" is a gene taken or copied from one organism and inserted into another organism. A transgene may be a gene that is foreign to the receiving organism or it may be a modified version of a native, or endogenous, gene.

DETAILED DESCRIPTION OF THE INVENTION

'E 499526' is a hybrid pepper cultivar with high yield potential. It is a medium vigorous plant that produces medium green immature fruit and light yellow mature fruit of a very small size jalapeno pepper size) but mild flavor (not hot). In addition, the plants are suitable for covered cultivation and open field growing. The hybrid cultivar has shown uniformity and stability for the traits, within the limits of environmental influence for the traits. The cultivar has been increased with continued observation for uniformity. No variant traits have been observed or are expected in 'E 499526'.

Hybrid pepper cultivar 'E 499526' has the following morphologic and other characteristics.

TABLE 1

VARIETY DESCRIPTION INFORMATION FOR E 499526

| | |
|---|---|
| GENERAL: | Type: Sweetbite |
| | Usage: Fresh market |
| | Type of culture: Covered cultivation and open field |
| PLANT: | Seedling, anthocyanin coloration of hypocotyl: Present |
| | Shortened internode: Absent |
| | Vigor: Medium |
| | Flower, attitude of peduncle: Non-erect |
| FRUIT: | Color before maturity: Green |
| | Intensity of color before maturity: Medium |
| | Length: 4 cm |
| | Diameter: 2 cm |
| | Predominant shape of longitundinal section: Trapezoid |
| | Color at maturity: Yellow |
| | Intensity of color at maturity: Light |
| | Predominant number of locules: Two and three |
| | Capsaicin in placenta: Absent |
| | Time of ripening (color change of fruits on 50% of plants): Medium |
| DISEASE RESISTANCE: | Tobamovirus pathotype $P_0$: Resistant |
| | Tobamovirus pathotype $P_1$: Susceptible |
| | Tobamovirus pathotype $P_{1-1}$: Susceptible |
| | Tobamovirus pathotype $P_{1-2-3}$: Susceptible |
| | Potato Virus Y pathotype $P_0$: Susceptible |
| | Potato Virus Y pathotype $P_1$: Susceptible |
| | Potato Virus Y pathotype $P_{1-2}$: Susceptible |
| | *Phytophthora capsici*: Susceptible |
| | Tomato Spotted Wilt Virus: Susceptible |
| | Cucumber Mosaic Virus: Susceptible |

FURTHER EMBODIMENTS OF THE INVENTION

This invention also is directed to methods for producing a pepper plant by crossing a first parent pepper plant with a second parent pepper plant wherein either the first or second parent pepper plant is a hybrid pepper plant of the cultivar 'E 499526'. Further, both first and second parent pepper plants can come from the hybrid pepper cultivar 'E 499526'. All plants produced using hybrid pepper cultivar 'E 499526' as a parent are within the scope of this invention, including plants derived from hybrid pepper cultivar 'E 499526'.

As used herein, the term plant includes plant cells, plant protoplasts, plant cell tissue cultures from which pepper plants can be regenerated, plant calli, plant clumps and plant cells that are intact in plants or parts of plants, such as embryos, pollen, ovules, flowers, leaves, stems, and the like.

As it is well known in the art, tissue culture of pepper can be used for the in vitro regeneration of pepper plants. Tissues cultures of various tissues of pepper and regeneration of plants therefrom are well known and published. By way of example, tissue cultures, some comprising organs to be used to produce regenerated plants, have been described in Burza et al., *Plant Breeding*. 1995, 114: 4, 341-345, Pellinen, *Angewandte Botanik*. 1997, 71: 3/4,116-118, Kuijpers et al., *Plant Cell Tissue and Organ Culture*. 1996, 46: 1, 81-83, Colijn-Hooymans et al., *Plant Cell Tissue and Organ Culture*. 1994, 39: 3, 211-217, Lou et al., *HortScience*. 1994, 29: 8, 906-909, Tabei et al., *Breeding Science*. 1994, 44: 1, 47-51, Sarmanto et al., *Plant Cell Tissue and Organ Culture* 31:3 185-193 (1992), Cade et al., *Journal of the American Society for Horticultural Science* 115:4 691-696 (1990), Chee et al., *HortScience* 25:7, 792-793 (1990), Kim et al., *HortScience* 24:4 702 (1989), Punja et al., *Plant Cell Report* 9:2 61-64 (1990). Pepper plants could be regenerated by somatic embryogenesis. It is clear from the literature that the state of the art is such that these methods of obtaining plants are "conventional" in the sense that they are routinely used and have a very high rate of success. Thus, another aspect of this invention is to provide cells which upon growth and differentiation produce pepper plants having the physiological and morphological characteristics of hybrid pepper cultivar 'E 499526'.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed cultivar.

Plant transformation involves the construction of an expression vector that will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed pepper plants, using transformation methods as described below to incorporate transgenes into the genetic material of the pepper plant(s).

Expression Vectors for Pepper Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals which confers resistance to kanamycin (Fraley et al., *Proc. Natl. Acad. Sci. U.S.A.*, 80:4803 (1983)). Another commonly used selectable marker gene is the hygromycin phosphotransferase gene which confers resistance to the antibiotic hygromycin (Vanden Elzen et al., *Plant Mol. Biol.*, 5:299 (1985)).

Additional selectable marker genes of bacterial origin that confer resistance to antibiotics include gentamycin acetyl transferase, streptomycin phosphotransferase, aminoglycoside-3'-adenyl transferase, the bleomycin resistance determinant (Hayford et al., *Plant Physiol.* 86:1216 (1988), Jones et al., *Mol. Gen. Genet.*, 210:86 (1987), Svab et al., *Plant Mol. Biol.* 14:197 (1990), Hille et al., *Plant Mol. Biol.* 7:171 (1986)). Other selectable marker genes confer resistance to herbicides such as glyphosate, glufosinate or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation that are not of bacterial origin include, for example, mouse dihydrofolate reductase, plant 5-enolpyruvylshikimate-3-phosphate synthase and plant acetolactate synthase (Eichholtz et al., *Somatic Cell Mol. Genet.* 13:67 (1987), Shah et al., *Science* 233:478 (1986), Charest et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984)).

In vivo methods for visualizing GUS activity that do not require destruction of plant tissues are available (Molecular Probes publication 2908, IMAGENE GREEN, p. 1-4 (1993) and Naleway et al., *J. Cell Biol.* 115:151 a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science* 263: 802 (1994)). GFP and mutants of GFP may be used as screenable markers.

Expression Vectors for Pepper Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in pepper. Optionally, the inducible promoter is operably linked to a nucleotide sequence encoding a signal sequence which is operably linked to a gene for expression in pepper. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *Proc. Natl. Acad. Sci U.S.A.* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., Mol. Gen. Genetics 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in pepper or the constitutive promoter is operably linked to a nucleotide sequence encoding a signal sequence which is operably linked to a gene for expression in pepper.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); PEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters

A tissue-specific promoter is operably linked to a gene for expression in pepper. Optionally, the tissue-specific promoter is operably linked to a nucleotide sequence encoding a signal sequence which is operably linked to a gene for expression in pepper. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Nat. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal Biochem.* 114:92-6 (1981).

According to a preferred embodiment, the transgenic plant provided for commercial production of foreign protein is pepper. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example Jones et al., Science 266:789 (1994) (cloning of the tomato Cf-9 gene for resistance to Cladosporium fulvum); Martin et al., Science 262:1432 (1993) (tomato Pto gene for resistance to Pseudomonas syringae pv. tomato encodes a protein kinase); Mindrinos et al., Cell 78:1089 (1994) (Arabidopsis RSP2 gene for resistance to Pseudomonas syringae).

B. A Bacillus thuringiensis protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., Plant Molec. Biol. 24:25 (1994), who disclose the nucleotide sequences of several Clivia miniata mannose-binding lectin genes.

D. A vitamin-binding protein such as avidin. See PCT application US 93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of Streptomyces nitrosporeus α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in Diploptera puntata). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper-accumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

L. A hydrophobic moment peptide. See PCT application WO 95/16776 (disclosure of peptide derivatives of tachyplesin which inhibit fungal plant pathogens) and PCT application WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-β, lytic peptide analog to render transgenic tobacco plants resistant to Pseudomonas solanacearum.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes That Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet* 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and Streptomyces hygroscopicus phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in Transgenic Research. 1999, 8: 1, 33-44 that discloses *Lactuca sativa* resistant to glufosinate. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes That Confer or Contribute to a Value-Added Trait, Such as:

A. Increased iron content of the pepper, for example by transforming a plant with a soybean ferritin gene as described in Goto et al., *Acta Horticulturae.* 2000, 521, 101-109.

B. Increased sweetness of the pepper by transferring a gene coding for monellin that elicits a flavor 100,000 times sweeter than sugar on a molar basis. See Penarrubia et al., *Biotechnology.* 1992, 10: 561-564.

4. Genes that Control Male-Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

Methods for Pepper Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation

One method for introducing an expression vector into plants is based on the natural transformation system of Agrobacterium. See, for example, Horsch et al., *Science* 227:1229 (1985), Curtis et al., *Journal of Experimental Botany.* 1994, 45: 279, 1441-1449, Torres et al., *Plant cell Tissue and Organic Culture.* 1993, 34: 3, 279-285, Dinant et al., *Molecular Breeding.* 1997, 3: 1, 75-86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of Agrobacterium vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Russell, D. R., et al. *Pl. Cell. Rep.* 12(3, January), 165-169 (1993), Aragao, F. J. L., et al. *Plant Mol. Biol.* 20 (2, October), 357-359 (1992), Aragao, F. J. L., et al. *Pl. Cell. Rep.* 12(9, July), 483-490 (1993). Aragao, *Theor. Appl. Genet.* 93: 142-150 (1996), Kim, J.; Minamikawa, T. *Plant Science* 117: 131-138 (1996), Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.,* 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Saker, M.; Kuhne, T. *Biologia Plantarum* 40(4): 507-514 (1997/98), Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994). See also Chupean et al., *Biotechnology.* 1989, 7: 5, 503-508.

Following transformation of pepper target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic pepper line. Alternatively, a genetic trait which has been engineered into a particular pepper cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Single-Gene Conversions

When the terms pepper plant, cultivar or pepper line are used in the context of the present invention, this also includes any single gene conversions of that line. The term "single gene converted plant" as used herein refers to those pepper plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term "backcrossing" as used herein refers to the repeated crossing of a hybrid progeny back to one of the parental pepper plants for that line, backcrossing 1, 2, 3, 4, 5, 6, 7, 8 or more times to the recurrent parent. The parental pepper plant which contributes the gene for the desired characteristic is termed the nonrecurrent or donor parent. This terminology refers to the fact that the nonrecurrent parent is used one time in the backcross protocol and therefore does not recur. The parental pepper plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a pepper plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, male sterility, modified fatty acid metabolism, modified carbohydrate metabolism, herbicide resistance, nematode resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,777,196, 5,948,957 and 5,969,212, the disclosures of which are specifically hereby incorporated by reference.

Tissue Culture

Further reproduction of the variety can occur by tissue culture and regeneration. Tissue culture of various tissues of pepper and regeneration of plants therefrom is well known and widely published. For example, reference may be had to Teng et al., *HortScience.* 1992, 27: 9, 1030-1032 Teng et al., *HortScience.* 1993, 28: 6, 669-1671, Zhang et al., *Journal of Genetics and Breeding.* 1992, 46: 3, 287-290, Webb et al., *Plant Cell Tissue and Organ Culture.* 1994, 38: 1, 77-79, Curtis et al., *Journal of Experimental Botany.* 1994, 45: 279, 1441-1449, Nagata et al., *Journal for the American Society for Horticultural Science.* 2000, 125: 6, 669-672, and Ibrahim et al., *Plant Cell, Tissue and Organ Culture.* (1992), 28 (2): 139-145. It is clear from the literature that the state of the art is such that these methods of obtaining plants are routinely used and have a very high rate of success. Thus, another aspect of this invention is to provide cells which upon growth and differentiation produce pepper plants having the physiological and morphological characteristics of the hybrid 'E 499526'.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a pepper plant by crossing a first parent pepper plant with a second parent pepper plant wherein the first or second parent pepper plant is a pepper plant of cultivar 'E 499526'. Further, both first and second parent pepper plants can come from pepper cultivar 'E 499526'. Thus, any such methods using pepper cultivar 'E 499526' are part of this invention: selfing, backcrosses, hybrid production, crosses to populations, and the like. All plants produced using pepper cultivar 'E 499526' as at least one parent are within the scope of this invention, including those developed from cultivars derived from pepper cultivar 'E 499526'. Advantageously, this pepper cultivar could be used in crosses with other, different, pepper plants to produce the first generation ($F_1$) pepper hybrid seeds and plants with superior characteristics. The cultivar of the invention can also be used for transformation where exogenous genes are introduced and expressed by the cultivar of the invention. Genetic variants created either through traditional breeding methods using pepper cultivar 'E 499526' or through transformation of cultivar 'E 499526' by any of a number of protocols known to those of skill in the art are intended to be within the scope of this invention.

The following describes breeding methods that may be used with pepper hybrid 'E 499526' in the development of further pepper plants. One such embodiment is a method for developing progeny pepper plants in a pepper plant breeding program comprising: obtaining the pepper plant, or a part thereof, of cultivar 'E 499526', utilizing said plant or plant part as a source of breeding material, and selecting a pepper cultivar 'E 499526' progeny plant with molecular markers in common with cultivar 'E 499526' and/or with morphological and/or physiological characteristics selected from the characteristics listed in Table 1. Breeding steps that may be used in the pepper plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of pepper cultivar 'E 499526' progeny pepper plants, comprising crossing cultivar 'E 499526' with another pepper plant, thereby producing a population of pepper plants, which, on average, derive 50% of their alleles from pepper cultivar 'E 499526'. A plant of this population may be selected and repeatedly selfed or sibbed with a pepper cultivar resulting from these successive filial generations. One embodiment of this invention is the pepper cultivar produced by this method and that has obtained at least 50% of its alleles from pepper cultivar 'E 499526'.

One of ordinary skill in the art of plant breeding would know how to evaluate the traits of two plant varieties to determine if there is no significant difference between the two traits expressed by those varieties. For example, see Fehr and Walt, *Principles of Cultivar Development*, p 261-286 (1987). Thus the invention includes pepper cultivar 'E 499526' progeny pepper plants comprising a combination of at least two cultivar 'E 499526' traits selected from the group consisting of those listed in Table 1 or the cultivar 'E 499526' combination of traits listed in the Summary of the Invention, so that said progeny pepper plant is not significantly different for said traits than pepper cultivar 'E 499526' as determined at the 5% significance level when grown in the same environmental conditions. Using techniques described herein, molecular markers may be used to identify said progeny plant as a pepper cultivar 'E 499526' progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of pepper cultivar 'E 499526' may also be characterized through their filial relationship with pepper cultivar 'E 499526', as for example, being within a certain number of breeding crosses of pepper cultivar 'E 499526'. A breeding cross is a cross made to introduce new genetics into the progeny, and is distinguished from a cross, such as a self or a sib cross, made to select among existing genetic alleles. The lower the number of breeding crosses in the pedigree, the closer the relationship between pepper cultivar 'E 499526' and its progeny. For example, progeny produced by the methods described herein may be within 1, 2, 3, 4 or 5 breeding crosses of pepper cultivar 'E 499526'.

As used herein, the term "plant" includes plant cells, plant protoplasts, plant cell tissue cultures from which pepper plants can be regenerated, plant calli, plant clumps and plant cells that are intact in plants or parts of plants, such as fruit, leaves, pollen, embryos, cotyledons, hypocotyl, roots, root tips, anthers, pistils, flowers, seeds, stems and the like.

TABLES

In Table 2 that follows the morphologic and other characteristics of another hybrid pepper cultivar is shown. 'E 499524' is a hybrid pepper cultivar with high yield potential. It is a medium vigorous plant that produces medium green immature fruit and light red mature fruit of a very small size (jalapeno pepper size) but mild flavor (not hot). In addition, the plants are suitable for covered cultivation and open field growing. The hybrid cultivar has shown uniformity and stability for the traits, within the limits of environmental influence for the traits. The cultivar has been increased with continued observation for uniformity. No variant traits have been observed or are expected in 'E 499524'.

TABLE 2

| VARIETY DESCRIPTION INFORMATION FOR E 499524 | |
|---|---|
| GENERAL: | Type: Sweetbite |
| | Usage: Fresh market |
| | Type of culture: Covered cultivation and open field |
| PLANT: | Seedling, anthocyanin coloration of hypocotyl: Present |
| | Shortened internode: Absent |

TABLE 2-continued

VARIETY DESCRIPTION INFORMATION FOR E 499524

| | |
|---|---|
| | Vigor: Medium |
| | Flower, attitude of peduncle: Non-erect |
| FRUIT: | Color before maturity: Green |
| | Intensity of color before maturity: Medium |
| | Length: 5 cm |
| | Diameter: 2 cm |
| | Predominant shape of longitundinal section: Trapezoid |
| | Color at maturity: Red |
| | Intensity of color at maturity: Light |
| | Predominant number of locules: Two and three |
| | Capsaicin in placenta: Absent |
| | Time of ripening (color change of fruits on 50% of plants): Medium |
| DISEASE RESISTANCE: | Tobamovirus pathotype $P_0$: Resistant |
| | Tobamovirus pathotype $P_1$: Susceptible |
| | Tobamovirus pathotype $P_{1-1}$: Susceptible |
| | Tobamovirus pathotype $P_{1-2-3}$: Susceptible |
| | Potato Virus Y pathotype $P_0$: Susceptible |
| | Potato Virus Y pathotype $P_1$: Susceptible |
| | Potato Virus Y pathotype $P_{1-2}$: Susceptible |
| | *Phytophthora capsici*: Susceptible |
| | Tomato Spotted Wilt Virus: Susceptible |
| | Cucumber Mosaic Virus: Susceptible |

In Table 3 that follows the morphologic and other characteristics of another hybrid pepper cultivar is shown. 'E 499531' is a hybrid pepper cultivar with high yield potential. It is a medium vigorous plant that produces medium green immature fruit and medium orange mature fruit of a very small size (jalapeno pepper size) but mild flavor (not hot). In addition, the plants are suitable for covered cultivation and open field growing. The hybrid cultivar has shown uniformity and stability for the traits, within the limits of environmental influence for the traits. The cultivar has been increased with continued observation for uniformity. No variant traits have been observed or are expected in 'E 499531'.

TABLE 3

VARIETY DESCRIPTION INFORMATION FOR E 499531

| | |
|---|---|
| GENERAL: | Type: Sweetbite |
| | Usage: Fresh market |
| | Type of culture: Covered cultivation and open field |
| PLANT: | Seedling, anthocyanin coloration of hypocotyl: Present |
| | Shortened internode: Absent |
| | Vigor: Medium |
| | Flower, attitude of peduncle: Non-erect |
| FRUIT: | Color before maturity: Green |
| | Intensity of color before maturity: Medium |
| | Length: 4 cm |
| | Diameter: 2 cm |
| | Predominant shape of longitundinal section: Trapezoid |
| | Color at maturity: Orange |
| | Intensity of color at maturity: Medium |
| | Predominant number of locules: Two and three |
| | Capsaicin in placenta: Absent |
| | Time of ripening (color change of fruits on 50% of plants): Medium |
| DISEASE RESISTANCE: | Tobamovirus pathotype $P_0$: Resistant |
| | Tobamovirus pathotype $P_1$: Susceptible |
| | Tobamovirus pathotype $P_{1-1}$: Susceptible |
| | Tobamovirus pathotype $P_{1-2-3}$: Susceptible |
| | Potato Virus Y pathotype $P_0$: Susceptible |
| | Potato Virus Y pathotype $P_1$: Susceptible |
| | Potato Virus Y pathotype $P_{1-2}$: Susceptible |
| | *Phytophthora capsici*: Susceptible |
| | Tomato Spotted Wilt Virus: Susceptible |
| | Cucumber Mosaic Virus: Susceptible |

Deposit Information

A deposit of the Enza Zaden Beheer B.V. proprietary pepper hybrid E 499526 disclosed above and recited in the appended claims has been made with the American Type Culture Collection (ATCC), 10801 University Boulevard, Manassas, Va. 20110. The date of deposit was Apr. 13, 2010. The deposit of 2,500 seeds was taken from the same deposit maintained by Enza Zaden Beheer B.V. since prior to the filing date of this application. All restrictions will be removed upon granting of a patent, and the deposit is intended to meet all of the requirements of 37 C.F.R. §§1.801-1.809. The ATCC Accession Number is PTA-10817. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A hybrid pepper seed designated 'E 499526' wherein a representative sample of seed has been deposited under ATCC Accession No. PTA-10817.

2. A pepper plant produced by growing the seed of claim 1.

3. Pollen, ovule, seed, or fruit, of the plant, or a part of the plant, of claim 2.

4. A pepper plant having all of the physiological and morphological characteristics of the pepper plant of claim 2.

5. A Sweetbite pepper fruit with a diameter between 1.5 centimeters and 3 centimeters and a length between 3 centimeters and 7 centimeters, produced by a pepper plant grown from hybrid pepper seed 'E 499526', wherein a representative sample of said seed is deposited under ATCC Accession No. PTA-10817.

6. A tissue culture of cells produced from the pepper plant of claim 2, wherein said cells of the tissue culture are produced from a plant part selected from the group consisting of leaf, anther, pistil, stem, petiole, root, root tip, fruit, seed, flower, cotyledon, hypocotyl, embryo and meristematic cell.

7. A pepper plant regenerated from tissue culture of claim 6, wherein said pepper plant has all of the physiological and morphological characteristics of hybrid pepper 'E 499526'.

8. Pollen, ovule, seed, or fruit, of the plant, or a part of the plant, of claim 7.

9. A protoplast produced from the plant of claim 2.

10. A pepper plant regenerated from the protoplast of claim 9, wherein said pepper plant has all of the physiological and morphological characteristics of hybrid pepper 'E 499526'.

11. Pollen, ovule, seed, or fruit, of the plant, or a part of the plant, of claim 10.

12. A method for producing a pepper plant comprising crossing the pepper plant of claim 2 with a different pepper plant or with itself and harvesting the resultant pepper seed.

13. A method of producing a pepper plant wherein the method comprises transforming the pepper plant of claim 2 with a transgene.

14. A pepper plant produced by the method of claim 13.

15. Pollen, ovule, seed, or fruit, of the plant, or a part of the plant, of claim 14.

* * * * *